US005238824A

United States Patent [19]

Klesius

[11] Patent Number: 5,238,824

[45] Date of Patent: Aug. 24, 1993

[54] HYBRIDOMAS AND MONOCLONAL ANTIBODIES THEREFROM REACTIVE TOWARD ANTIGENS FROM EDWARDSIELLA ICTALURI

[75] Inventor: Phillip H. Klesius, Auburn, Ala.

[73] Assignee: The United States of America, as represented by the Secretary of Agriculture, Washington, D.C.

[21] Appl. No.: 431,348

[22] Filed: Nov. 3, 1989

[51] Int. Cl.[5] ............................................ A61K 35/14

[52] U.S. Cl. ............................ 435/70.21; 530/388.1; 530/387.1; 436/548

[58] Field of Search .................... 435/7, 240.27, 172.2; 436/512, 513, 548; 530/387, 857; 935/89, 103

[56] References Cited

PUBLICATIONS

J. A. Plumb et al., "An Assessment of the Antigenic Homogeneity of *Edwardsiella ictaluri* Using Monoclonal Anbibody," *J. Fish Dis.* 11:499-509 (1988).

P. Waterstrat et al., "Use of an Indirect Enzyme-Linked Immunosorbent Assay (ELISA) in the Detection of Channel Catfish, *Ictalurus punctatus* (Raninesque), Antibodies to *Edwardsiella ictaluri*," *J. Fish Dis.* 12:87-94 (1989).

Craig J. Lobb et al., "Immunoglobulin Light Chain Classes in a Teleost Fish," *J. Immunol.* 132(4):1917-1923 (Apr. 1984).

N. W. Miller et al., "Phylogeny of Lymphocyte Heterogeneity: Identification and Separation of Functionally Distinct Subpopulations of Channel Catfish Lymphocytes with Monoclonal Antibodies," *Dev. Comp. Immunol.* 11:739-747 (1987).

A. J. Ainsworth et al., "Use of Monoclonal Antibodies in the Indirect Fluorescent Antibody Technique (IFA) for the Diagnosis of *Edwardsiella ictaluri*," J. Fish Dis. 9:439-444 (1986).

Nigel Palmer letter to Phillip H. Klesius dated May 13, 1991, disclosing mailing date to subscribers of J. Fish Dis. 11(6) (Nov. 1988).

Ainsworth et al., Biol. Abstr. 83(6) 1987, 55627, "Use of Monoclonal Antibodies in the Indirect Fluorescent Antibody Technique for the Diagnosis of *Edwardsiella ictaluri*".

*Primary Examiner*—Robert J. Hill, Jr.
*Assistant Examiner*—Laurie Scheiner
*Attorney, Agent, or Firm*—M. Howard Silverstein; John D. Fado; Curtis P. Ribando

[57] ABSTRACT

A hybridoma cell line produces an antibody with reactivity directed specifically to immunodominant antigens from the catfish pathogen *Edwardsiella ictaluri*, the antigens having molecular weights of about 14,000, 39,000, 48,000, 60,000, 66,000, 83,000, and 93,000 daltons. This antibody is specific for proteins of *E. ictaluri* but not for other catfish pathogens. It is therefore useful for the positive identification of *E. ictaluri* from body fluids and tissue of catfish and for identification and purification of the reactive immunodominant antigens.

2 Claims, No Drawings

HYBRIDOMAS AND MONOCLONAL ANTIBODIES THEREFROM REACTIVE TOWARD ANTIGENS FROM EDWARDSIELLA ICTALURI

BACKGROUND OF THE INVENTION

1. Field of the Invention

*Edwardsiella ictaluri*, the causative agent of enteric septicaemia of catfish (ESC), has become widely spread throughout the catfish industry since its original isolation in 1977 [Hawke, J. Fish. Res. Board Canada 36:1508–1512 (1979); Hawke et al., Int. J. Syst. Bacteriol. 31: 396–400 (1981)]. This pathogen has been isolated from cultured channel catfish in most areas of the United States where this species is cultured and from walking catfish in Thailand [Kasornchandra et al., J. Fish Dis. 10: 137—138 (1987)]; therefore, it is likely that this organism has a wide geographical range.

This invention relates to hybridoma cell lines which produce monoclonal antibodies (Mabs) having reactivity specifically toward an *E. ictaluri* antigen of a molecular weight of about 14,000, 39,000, 48,000, 60,000, 66,000, 83,000, and 93,000 daltons. The Mabs are useful for diagnosis of *E. ictaluri* in body fluids and tissues of catfish and are promising reagents for identification and purification of the aforementioned antigens from *E. ictaluri*. The purified antigens will be useful in diagnosis and vaccination of *E. ictaluri.*

2. Description of the Prior Art

Recently, Plumb et al. [J. Fish Dis. 11: 499–509 (1988)] reported the use of channel catfish anti-*E. ictaluri* serum to identify distinct antigens of *E. ictaluri.* The catfish antibodies were reported to be reactive with antigens of approximately 34,000 and 60,000 daltons and were believed to be dominant immunoproteins or immunodominant antigens of *E. ictaluri.*

E. ictaluri is reported to be used as whole cells in an enzyme-linked immunoabsorbent assay (ELISA) to detect *E. ictaluri* antibodies in infected catfish [Waterstrat et al., J. Fish Dis. 12: 87–95 (1989)]. No evidence was presented for *E. ictaluri* specificity by ELISA using whole cells as antigen.

SUMMARY OF THE INVENTION

I have now constructed a hybridoma cell line which produces Mabs that bind selectively to antigens from *E. ictaluri* having a molecular weight of about 14,000, 39,000, 48,000, 60,000, 66,000, 83,000, and 93,000 daltons.

It is an objective of this invention to provide murine hybridoma cell lines which produce monoclonal antibodies specific for *E. ictaluri* and its antigens.

It is a further objective of this invention to provide monoclonal antibodies as immunochemical reagents for the identification and purification of the aforementioned antigens, as reagents for diagnosis of *E. ictaluri*, and for the development of vaccines against *E. ictaluri.*

Other objects and advantages of this invention will become readily apparent from the ensuing description.

DEPOSIT OF BIOLOGICAL MATERIAL

The cloned hybridoma cell line designated AA224 was deposited on Jul. 21, 1989, under the conditions of the Budapest Treaty with the American Type Culture Collection, Rockville, Md., and has been assigned number ATCC HB10183.

DETAILED DESCRIPTION OF THE INVENTION

The hybrid-cell or hybridoma of the invention was produced by fusion of a mouse myeloma cell line (P3X63-Ag8.653) and a spleen cell from a mouse (BALB/c), according to the procedure described by Kohler and Milstein [Nature 256: 495: 497 (1975)]. The mouse spleen cell donor had been previously injected with immunoaffinity-purified antigens from *E. ictaluri* covalently linked to catfish immunoglobulin specific for *E. ictaluri* immunodominant antigens described further in Example 3. The cells were fused by standard methods using polyethylene glycol.

Hybrids were selected in a medium which contained hypoxanthine/aminopterine/thymidine (HAT) as described by Littlefield [Science 145: 709–710 (1964)], and fused cells were plated in wells of tissue culture plates. Approximately 14–15 days after fusion, culture supernatant was collected from actively growing hybridoma colonies and screened for antibody production by ELISA using semipurified antigen. Hybridoma cell lines expressing positive screening reactions were cloned by limiting dilution to obtained single cells. Wells were monitored for the appearance of cell colonies, and culture supernatants from wells with only one colony were again screened by ELISA as above. Positive-reacting hybridomas were tested for monoclonality by Ouchterlony analysis [Ouchterlony Prog. Allergy 5: 1–406 (1958). From these hybridomas, a cell line designated as AA224 was selected which produced an IgM immunoglobulin Mab having specific reactivity with antigens from *E. ictaluri* having a molecular weight of about 14,000, 39,000, 48,000, 60,000, 66,000, 83,000, and 93,000 daltons as demonstrated by Western blot analysis. The hybrid cell selected was twice cloned and preserved by freezing in liquid nitrogen.

The Mabs produced by the AA224 hybridoma cell line bind selectively to antigens from *E. ictaluri* present in body fluids and tissues of catfish infected with *E. ictaluri*. These Mabs are useful as immunochemical reagents for the purification of immunogenic proteins and for specific probes of protein structure. Immunoaffinity chromatography utilizing these Mabs will be useful in preparation of *E. ictaluri* antigens for diagnostic and vaccine reagents. Thus, the AA224 Mabs which bind to *E. ictaluri* antigens having a molecular weight of about 14,000, 39,000, 48,000, 60,000, 66,000, 83,000, and 93,000 daltons as well as the antigens themselves which react with the antibodies are encompassed by the invention.

The AA224 Mab may be used to purify the aforementioned antigens by means of an immunoaffinity column or a solid immunoabsorbent bead with the AA224 Mab according to known procedures. Thus, the invention allows purification of antigens which cause antibody or immune responses that may be diagnostic and protective. The AA224 Mab may also be used in the development of an anti-idiotypic antibody.

The following examples are intended only to further illustrate the invention and are not intended to limit the scope of the invention which is defined by the claims.

EXAMPLE 1

Collection of Fish Serum

Channel catfish 15–18 in long were collected from ponds at the Department of Fisheries and Allied Aquacultures, Alabama Agricultural Experiment Station, Auburn University or from a commercial fish farmer (Salem. Ala.). The fish were immunized with $5\times10^5$ whole cells of live *E. ictaluri*. After 30–40 da, the fish were bled from the caudal vein or heart, and the serum was collected from clotted blood.

EXAMPLE 2

Preparation of *E. ictaluri* Antigen Extract

Whole cells of *E. ictaluri* isolate ATCC 3320 were obtained from BHI broth culture incubated at 25° C. for 24–49 hr. The cell suspension was centrifuged at 300×g for 30 min and supernatant was discarded. The bacterial cells were resuspended in 10 ml of 10 mM Tris-5 mM $MgCl_2$, pH 7.5. The cells in suspension were then lysed by sonication (5–10 1-min cycles). The lysate was centrifuged at 3000 g for 1 min to remove any unbroken cells. The lysate was again centrifuged at 3000 g for 30 min, and the supernatant was drawn off.

The recovered supernatant was termed "cell supernatant" and was used an antigen in ELISA, SDS-PAGE, and Western blot analysis. The cell supernatant antigen was also used as a starting antigen preparation for affinity purification of specific *E. ictaluri* antigens.

The pellet from the cell lysate was resuspended in 1–2 ml of 10 mM Tris-5 mM $MgCl_2$ (pH 8.0) containing 2Trion×100 and allowed to stand at room temperature for 20 min. Following Triton extraction, the material was centrifuged at 3000 g for 30 min. The recovered supernatant was saved and termed "extract supernatant." The cell extract supernatant was also used as antigen for the purpose stated above for the cell supernatant antigen.

In the above extractions, all centrifugation steps were done at 4° C. whereas all other steps at room temperature (about 25° C.)

EXAMPLE 3

Preparation of Semipurified Antigens from *E. ictaluri*

Pooled immune serum from Example 1 was precipitated by ammonium sulfate at 45% saturation. The antibody precipitates collected by centrifugation at 12,000×g for 10 min were dissolved in, and dialyzed against, 0.05M Tris-HCl, pH 8.5, containing 0.9M NaCl, 0.01EDTA, and 0.22% $NaN_2$ for 3–4 da with twice daily charges of buffer. The material was chromatographed on an affinity column containing catfish anti-H monoclonal (E-8) to purify catfish antibody or immunoglobulin. The affinity purified catfish antibody having specificity for *E. ictaluri* antigens was then coupled onto CNBr-activated sepharose 4B beads according to the procedure recommended by the manufacturer and placed in a column. The *E. ictaluri* cell supernatant antigen extract was added to the immune affinity column containing the immobilized catfish antibody, and unbound material was washed off the column with phosphate buffered saline (PBS). The bound antigens were eluted with 0.2M glycine, pH 2.5, into 1.0M Tris buffer, pH 7.5. The affinity semipurified antigens were dialyzed and concentrated using ultrafiltration apparatus with a 10,000 dalton filter. These semipurified antigens from *E. ictaluri* were used to immunize the mice for Mab production and ELISA screening assays.

EXAMPLE 4

Hybridoma and Mab Production

Male Balb/c mice (6–8 wk old) were subcutaneously injected at several sites with 200 μg of the semipurified antigen from Example 3 emulsified 1:1 in Freund's Complete Adjuvant. A subcutaneous injection with the same antigen-adjuvant was given 6 da later. After 10–14 da, a final injection of 600 μg in 0.25 ml PBS was given by intravenous injection. Spleens were removed from the mice 3 da later and fused with P3/X63/Ag8.653 mouse myeloma cells. The resulting 72 fusion products produced by polyethylene glycol 4000 fusion were grown in hypoxanthine, aminopterine, thymidine (HAT)-selective RPMI-1640 supplemented with 15% fetal calf serum in 24-well culture plates [Littlefield, supra].

Cell supernatants were initially screened for antibodies by indirect ELISA, using horseradish peroxidase labeled anti-mouse immunoglobulin antisera and cell supernatant antigen as follows. A microtitration plate was contacted with a solution of 100 μl/well containing 1 μg of protein per ml of cell supernatant antigen for 60 min to allow the antigen to attach to the wells. The wells were washed three times with PBS-0.05% Tween 20 (PSB-T). PBS containing 2% immunoglobulin-free horse serum (blocking buffer) was added, and the wells were incubated for 30 min before PBS-T washing (3×). Wells were reacted with a dilution of horseradish peroxidase (HRP)-labeled anti-mouse IgG. Positive reactions were visualized by color development with 3% hydrogen peroxide and O-phenylenediamine dihydrochloride (40 mg/100 ml) in 0.1M citric acid buffer.

Two hybridomas producing antibodies to *E. ictaluri* antigens were cloned by limiting dilution and subclassed by immunodiffusion using isotype specific anti-mouse antisera. Secreting hybridoma cell line AA224 was selected for expansion. Culture supernatants from serially passaged hybridomas were stored at −70° C. until used.

EXAMPLE 5

Ascites

The hybridoma AA224 from Example 4 was grown as ascites in the peritoneal cavity of Balb/c mice primed with "Pristane" 12–14 da prior to the injection of 2 million hybridoma cells. Ascites fluid taken from the intraperitoneal cavity was made cell-free by centrifugation at 800×g for 15 min. Ultrafiltration technique recommended by the manufacturer (Amicon, Danver, Mass.) with a 100,000 dalton membrane was used to isolate IgM from ascites. The presence of AA224 was confirmed by indirect ELISA essentially as described in Example 4.

EXAMPLE 6

Immunfluorescence

The Mabs produced in Example 5 were screened by indirect immunofluorescent assay (IFA), which was used to demonstrate a potential fluorescent reaction of *E. ictaluri* whole cells at a magnification of 100×. The AA224 Mab gave a strong surface fluorescent reaction upon incubation with the cells. The results presented in Table I show the specificity of AA224 Mab for *E. ictaluri* by IFA.

EXAMPLE 7

Immunoaffinity purification of antigens from *E. ictaluri*

Mab AA224 isolated from ascites in Example 5 was coupled onto CnBr-activated Sephase 4B beads and packed into an immunoaffinity column according to the procedure recommended by the manufacturer. *E. ictaluri* cell supernatant or extract supernatant antigen prepared as described in Example 2 was added to the immunoaffinity column containing the immobilized Mab, and the unbound material was washed off the column with PBS. The bound antigens were eluted with 0.2M glycine, pH 2.5, into 1.0M Tris buffer, pH 7.5. The resultant affinity-purified antigens were dialyzed and concentrated using an ultrafiltration apparatus with a 1,000-dalton filter (Amicon, Danver, Mass.). The procedure was repeated with cell supernatant and extract supernatant antigen of *E. tarda* and *A. hydrophilus.*

EXAMPLE 8

ELISA of Immunized Catfish

Sera was collected for channel catfish immunized with *E. ictaluri, E. tarda*, or *Aeromonas hydrophilus.* Example 7 were reacted with the sera, and the reaction products were assayed by ELISA following the procedure described by Engvall et al. [J. Immunol. 109(1): 129–135 (1972)]. The results are reported in Table II below.

TABLE I

IFA Reactions of Bacteria Associated with Channel Catfish Infections Mediated by Mab AA224

| Bacteria[a] | Titer[b] |
|---|---|
| *Edwardsiella ictaluri* | 15 |
| *Edwardsiella tarda* | — |
| *Aeromonas hydrophila* | — |
| *Pseudomonas fluorescens* | — |
| *Vibrio anguilarum* | — |
| *Yersinia ruckeri* | — |
| *Moraxella sp.* | — |
| *Streptococcus sp.* | — |
| *Bacillus sp.* | — |

[a]Bacterial isolates were obtained from Fish Health Diagnostic Laboratory, Department of Fisheries and Allied Aquacultures, Alabama Agricultural Experiment Station, Auburn University.
[b]Protein concentration, μg of Mab AA224 giving a clearly readable fluoresence. Negative sign is no reaction at a protein concentration of 125 μg Mab AA224.

TABLE II

ELISA Analysis of *E. ictaluri* Immunoaffinity Antigens Reacted with Fish Sera

| Fish immunized | Fish No. | ELISA* optical density |
|---|---|---|
| *E. ictaluri* | 1 | 0.028 |
| | 2 | 0.092 |
| | 3 | 0.176 |
| | 4 | 0.059 |
| | 5 | 0.083 |
| *E. tarda* | 1 | 0.019 |
| | 2 | 0.005 |
| | 3 | 0.006 |
| | 4 | 0.004 |
| | 5 | 0.004 |
| *A. hydrophilus* | 1 | 0.008 |
| | 2 | 0.001 |
| | 3 | 0.014 |
| | 4 | 0.007 |
| | 5 | 0.021 |

*Fish serum diluted to 1/40. Positive agglutination titers were found in all fish against immunizing antigen. Negative serum control was 0.009, and positive serum control was 0.820.

EXAMPLE 9

ELISA of Infected Catfish

Sera was collected from five nonimmunized channel catfish infected with *E. ictaluri.* Immunoaffinity antigens from *E. ictaluri* prepared as described in Example 7 were reacted with the sera and the reaction products were assayed by ELISA as in Example 8. The results are reported in Table III below.

TABLE III

ELISA Analysis of Immunoaffinity Antigens Reacted with Sera from *E. ictaluri*-Infected Catfish

| Infected fish | ELISA* optical density |
|---|---|
| 1 | 0.534 |
| 2 | 0.644 |
| 3 | 0.322 |
| 4 | 0.347 |
| 5 | 0.304 |

*Serum dilution was 1/40.

EXAMPLE 10

Antigen ELISA

An antigen ELISA was conducted by sensitizing a microtitration plate with 50 μl of solution containing 40 μl of catfish serum and 10 μl of 0.06M carbonate buffer (pH 9.6) and incubated for 1 hr. The plate was washed three times with PBS (pH 7.2) containing 0.05% Tween. To duplicate wells, 50 μl of an optimal dilution of horseradish peroxidase enzyme-labeled AA224 Mab was added. After incubation of 1 hr, the plate was washed as above. Positive reactions were visualized by color development with 3% hydrogen peroxide and O-phenylenediamine dihydrochloride (40 mg/100 ml) in 0.1M citric acid buffer. The results are shown in Table IV below.

EXAMPLE 11

SDS-PAGE and Western Blot

Gradient gels of 10–15% SDS-PAGE (Pharmacia, Piscataway, N.J.) or 0.75 mm SDS-PAGE discontinuous vertical slab gel (12%) with a 3% stacking polyacylamide gel [Haverstein et al., Devel. Comp. Immunol. 12: 773–785 (1988)] were used. Samples containing the *E. ictaluri* antigens were prepared according to the method described in Example 2 for cell and extract supernatant. Samples containing the antigens were prepared in sample buffer at concentrations of 0.5 to 1.0 mg/ml, heated in boiling water for 4 min. Electrophoresis was performed at a constant 350 v and 10 mA at 15°–25° C. Gels not used for Western blotting were stained by Coomassie Brilliant Blue R250 stain. Molecular weight estimations of the antigen were made by incorporation of prestained molecular weight markers into electrophoresis runs.

After SDS-PAGE, proteins were transferred to nitrocellulose using Pharmacia apparatus. Electrophoretic transfer was done at a constant 20 v and 25 mA for 2–4 hr. The nitrocellulose strips were blocked with a solution of 2% horse serum. The block strips were incubated in Mab solutions of 1 hr, washed with PBS/"Tween", and then incubated for 1 hr with HPR-labeled anti-mouse IgG for 1 hr. The strips were washed with PBS/"Tween", and the color was developed with 0.05% 4-chloro 1-naphthol and 0.015% $H_2O_2$.

Monoclonal antibody AA224 showed recognition of antigens of about 14,000, 39,000, 48,000, 60,000, 66,000, 83,000, and 93,000 daltons from *E. ictaluri* in the Western blot. The 39,000- and 60,000-dalton antigens were the predominant bands.

The AA224 hybridoma secretes IgM subclass monoclonal antibody. This Mab was useful in immunoaffinity purification of immunodominant antigens from *E. ictaluri* and detection of *E. ictaluri* or its antigen in tissues from catfish infected with *E. ictaluri.*

It is understood that the foregoing detailed description is given merely by way of illustration and that modification and variations made be made therein without departing from the spirit and scope of the invention.

TABLE IV

ELISA Reactivity of Serum from Catfish Infected with *E. ictaluri* Probed with AA224 Mab

| Fish | Sera* from Infected | Sera* from Noninfected |
|---|---|---|
| 1 | 0.171** | 0.000 |
| 2 | 0.147 | 0.025 |
| 3 | 0.257 | 0.016 |
| 4 | 0.096 | 0.009 |
| 5 | 0.670 | 0.021 |
| 6 | 0.239 | 0.035 |
| 7 | 1.173 | 0.019 |
| 8 | 0.507 | 0.030 |
| 9 | 0.058 | 0.001 |
| 10 | 0.064 | 0.000 |

*40 μl of undiluted serum plus 10 μl carbonate buffer for 1-hr incubation.
**Optical density reading; control 0.030.

I claim:

1. A hybridoma cell line capable of producing a monoclonal antibody which binds with antigens of *Edwardsiella ictaluri* having molecular weights of about 14,000, 39,000, 48,000, 60,000, 66,000, 83,000, and 93,000 daltons, wherein said hybridoma cell line has the identifying characteristics of ATCC. No. HB10183.

2. A monoclonal antibody capable of specifically binding with antigens of *Edwardsiella ictaluri* having molecular weights of about 14,000, 39,000, 48,000, 60,000, 66,000, 83,000, and 93,000 daltons, wherein said monoclonal antibody is produced by a hybridoma cell line having the identifying characteristics of ATCC. No. HB10183.

* * * * *